United States Patent
Delhomme et al.

[11] Patent Number: 5,809,163
[45] Date of Patent: Sep. 15, 1998

[54] METHOD OF CHARACTERIZING TEXTURE HETEROGENEITIES OF GEOLOGICAL FORMATIONS TRAVERSED BY A BOREHOLE

[75] Inventors: Jean-Pierre Delhomme, Boulogne Billancourt; Jean-François Rivest, Fontenaibleau, both of France

[73] Assignee: Schlumberger Technology Corporation, Ridgefield, Conn.

[21] Appl. No.: 390,268

[22] Filed: Feb. 16, 1995

Related U.S. Application Data

[63] Continuation of Ser. No. 178,581, Jan. 7, 1994, abandoned, which is a continuation of Ser. No. 840,788, Feb. 24, 1992, abandoned.

[30] Foreign Application Priority Data

Feb. 26, 1991 [FR] France ................................. 91 02267

[51] Int. Cl.⁶ .......................................................... G01V 1/00
[52] U.S. Cl. .............................. 382/109; 364/422; 367/69
[58] Field of Search .............................. 382/109; 348/85; 364/422; 367/35, 69; 324/323, 366, 367, 355; 73/151, 152

[56] References Cited

U.S. PATENT DOCUMENTS

| | | | |
|---|---|---|---|
| 4,567,759 | 2/1986 | Ekstrom et al. | 73/152 |
| 4,703,277 | 10/1987 | Kenyon et al. | 324/323 |
| 4,769,606 | 9/1988 | Vinegar et al. | 324/366 |
| 4,882,763 | 11/1989 | Buchan et al. | 382/1 |
| 4,885,723 | 12/1989 | Havira et al. | 367/35 |
| 5,012,193 | 4/1991 | Chen | 324/366 |
| 5,038,378 | 8/1991 | Chen | 382/1 |
| 5,162,994 | 11/1992 | Torres | 364/422 |

FOREIGN PATENT DOCUMENTS

| | | |
|---|---|---|
| 0 110 750 | 1/1985 | European Pat. Off. . |
| 0 159 944 | 5/1988 | European Pat. Off. . |
| 2 647 570 | 11/1990 | France . |

OTHER PUBLICATIONS

J. Serra, Image Analysis and Mathematical Morphology, *Academic Press Inc. Ltd.*, London (1982), pp. 434–463.

F. Meyer and S. Beucher, *Morphological Segmentation*, Journal of Visual Communication and Image Representation, vol. 1, No. 1, pp. 21–46, Sep. 1990.

*Primary Examiner*—Leo Boudreau
*Assistant Examiner*—Chris Kelley
*Attorney, Agent, or Firm*—Martin D. Hyden; Brigitte L. Jeffery; Keith G. W. Smith

[57] ABSTRACT

A method of characterizing texture heterogeneities in a geological formation traversed by a borehole. The method records an image of the borehole wall such as that provided by Schlumberger's Formation Microscanner (FMS) apparatus, representative of variations in a physical parameter of the formation in the longitudinal direction of the borehole and around the periphery of the wall. Geological objects are extracted from the image corresponding to a determined morphological type of heterogeneity. The variation in at least one attribute defined for this type of heterogeneity in the longitudinal direction of the borehole is determined. The invention is particularly applicable to vug detection.

24 Claims, 5 Drawing Sheets

METHOD OF CHARACTERIZING TEXTURE HETEROGENEITIES OF GEOLOGICAL FORMATIONS TRAVERSED BY A BOREHOLE

This application is a file wrapper continuation of Ser. No. 08/178,581, filed Jan. 7, 1994, abandoned, which is a file wrapper continuation of parent application Ser. No. 07/840,788, filed Feb. 24, 1992, abandoned.

BACKGROUND OF THE INVENTION

The invention relates to the investigation of geological formations traversed by a borehole, and more particularly to a method for characterizing texture heterogeneities of the formations.

It is known that texture heterogeneities in rocks (vugs, nodules, etc.) have an influence on the porosity and the permeability of formations. In hydrocarbon reservoirs, these are key parameters for evaluating production potential. It is therefore important to be able to characterize such heterogeneities.

SUMMARY OF THE INVENTION

The present invention provides a method of characterizing such heterogeneities.

The invention is based on automatic processing of an image of the borehole wall. Since the introduction of Schlumberger's formation microscanner apparatus (FMS), such an image has been available with a resolution of better than one centimeter. This apparatus provides an electrical image of the wall of a borehole, i.e. an image in which intensity is a function of formation resistivity.

According to the invention, an image of the borehole wall is recorded. The image includes variations of the formation in a physical parameter in the longitudinal direction of the borehole and around the periphery of the wall. Geological objects corresponding to a determined morphological type of heterogeneity are extracted from the image. The variation in the longitudinal direction of the borehole is determined for at least one attribute defined for this type of heterogeneity. The method of the invention is advantageously applicable to vug detection.

Various attributes may be envisaged, on their own or advantageously in combination: fraction of the image area occupied by vugs; mean area of vugs; and the degree of connectivity between vugs.

BRIEF DESCRIPTION OF THE DRAWINGS

The file of this patent contains at least one drawing executed in color.

The invention will be well understood on reading the following description made with reference to the accompanying drawings. In the drawings.

DESCRIPTION OF THE PREFERRED EMBODIMENTS

Figure 1:
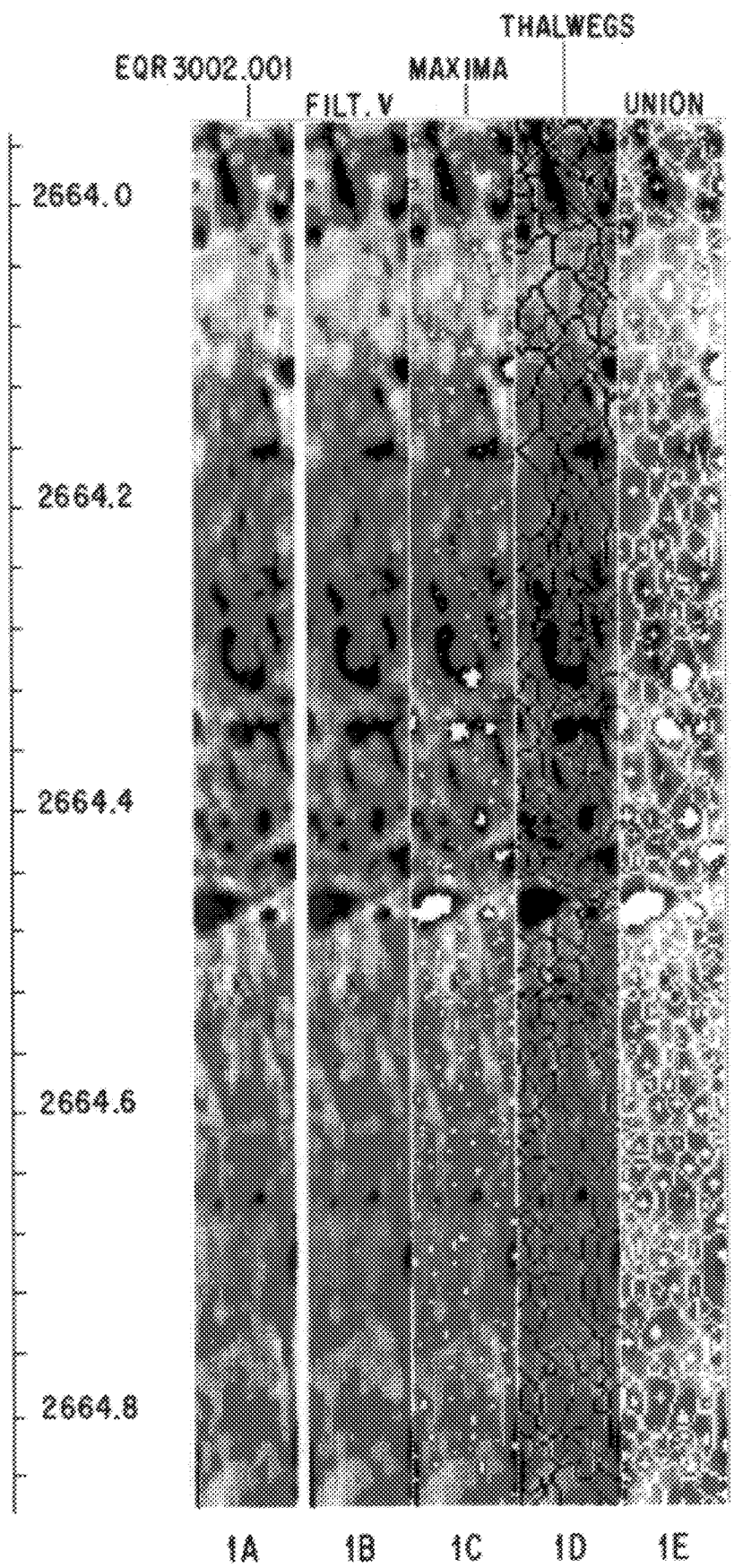
FIG. 1A is an image of the wall of a borehole obtained using an FMS apparatus.
FIGS. 1B to 1E show the results obtained during successive processing stages, in a first part of the processing.
Figure 5:
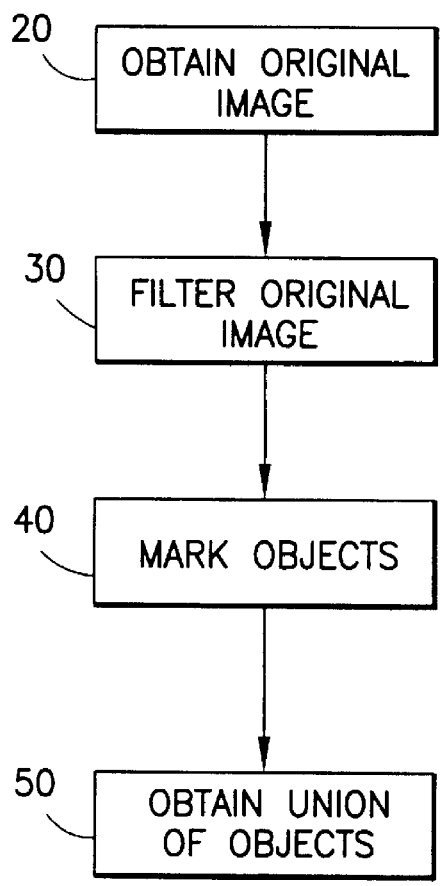
FIG. 5 and FIG. 6 are flow charts depicting the processing steps.

FIG. 1A shows the wall of a borehole over a length of about 80 centimeters and was obtained using Schlumberger's formation microscanner (FMS) apparatus. That apparatus includes pads each provided with a dense array of electrodes, with electrode size and inter-electrode spacing being of the order of 1 centimeter or less. During a measurement operation which is performed by moving the apparatus uphole by means of a cable, the pads are applied against respective sectors of the borehole wall. The electrical current emitted by an electrode is representative of the resistivity of the formation facing that electrode. The set of measurements provided by the electrodes on a pad are combined to produce an electrical image of the borehole wall on a gray scale: black corresponds to low resistivity and white to high resistivity (FIG. 5, Block 20). The lateral dimension of the image corresponds to the circumferential direction of the borehole and is limited to the angular sector covered by the array of electrodes.

The image processing stages described below use operators that are based on principles of mathematical morphology and which make it possible to simplify an image while retaining its essential morphological characteristics. The operators in question are described in the literature and there is no need to explain them in detail. References used in the present description are the following: J. Serra, "Image analysis and mathematical morphology", Academic Press, London, 1982 (hereinafter "Serra"), and F. Meyer & S. Beucher, "Morphological segmentation", Journal of Visual Communication and Image Representation, Vol. 1, No. 1, pp. 21–46, September 1990 (hereinafter "Meyer et al.").

In the following description, a topological metaphor is used to characterize the components of an image: image points having highest conductivity values are called "summits", paths interconnecting summits are called "cresdines", and paths interconnecting low value zones are called "thalwegs". Finally, the notion of a water parting or "divide" is used to designate the frontier between "watersheds" within which all downward paths converge towards a common "sink".

The image of FIG. 1A shows dark (i.e. highly conductive) zones corresponding to vugs. The operations illustrated by FIGS. 1B to 1E and 2B to 2D serve to extract zones that actually correspond to vugs from the starting image. The processing includes the "marking" in the image of objects of a morphology corresponding to a vug (a closed high conductivity zone), the "marking" of zones of low conductivity, and the delineation of vugs as defined by lines of higher contrast between the marked zones.

The original image is initially filtered to eliminate noise (FIG. 5, block 30). One suitable type of filtering uses the morphological closing operator (cf. Serra), with the structural element being a diamond shape of size 1. The filter image is shown in FIG. 1B.

Thereafter, summits are marked (FIG. 5, block 40). This marking is performed in appropriate manner by a morphological reconstruction technique (cf. Meyer et al.) enabling high value zones to be extracted. FIG. 1C bearing the legend "maxima" shows the result of this operation in the form of marked zones being superimposed in white on the image of FIG. 1B.

The stage illustrated by FIG. 1D is performed in parallel with summit marking. It consists in marking thalwegs (zones of low conductivity). This is performed appropriately by inverting (or "complementing", in accordance with Serra's terminology) the image of FIG. 1B so that high values then correspond to low conductivities, and then applying the inverted image to the operator which provides the divides (cf. Meyer et al.).

The resulting network of lines is marked in black, superimposed on the image of FIG. 1B.

The following stage, shown in FIG. 1E, achieves the union of the marked objects: summits and thalwegs (FIG. 5, block 50). FIG. 1E thus shows the summits shown in FIG. 1C and the thalwegs shown in FIG. 1D superimposed on the image of FIG. 1B. This union is achieved under the condition that any contact between summits and thalwegs be avoided. This stage is performed as follows: the image formed of the set of summits is dilated (cf. Serra), the image formed of the set of thalwegs is dilated, the dilated image of the thalwegs is inverted, and an intersection is performed between said inverted image and the dilated image of the summits.

Figure 2:
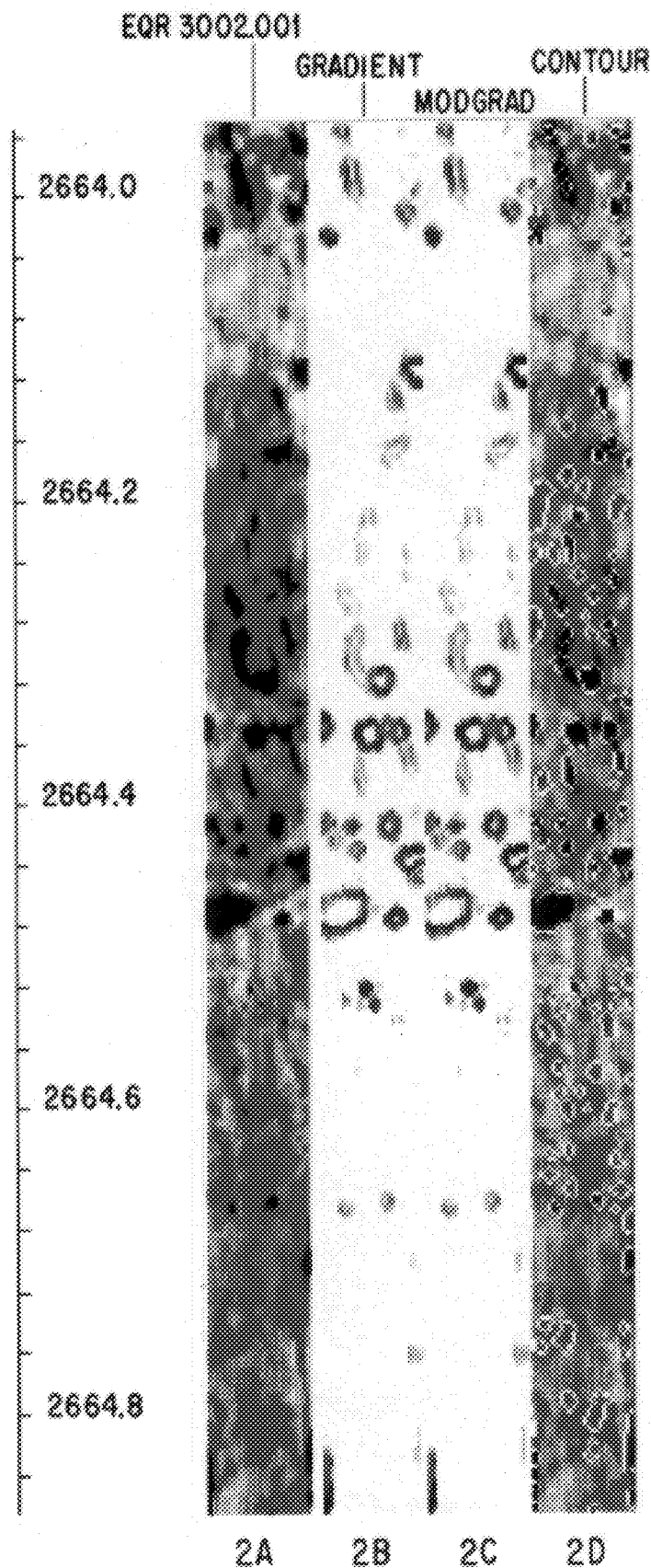
FIGS. 2A to 2D show the stages of a second part of the processing for showing up vugs, with FIG. 2A reproducing the image of FIG. 1A for the sake of clarity.
Figure 6:
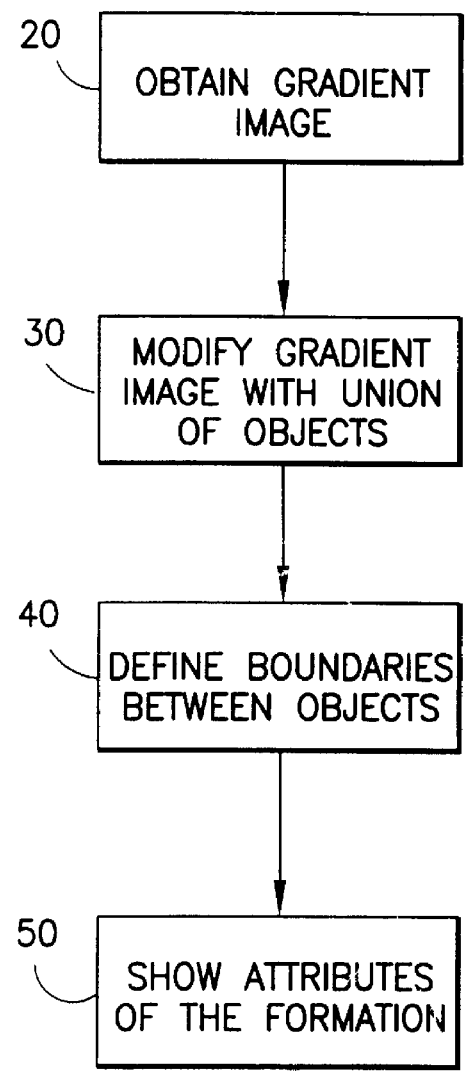

In parallel with this first portion of the processing, a gradient image as shown in FIG. 2B is produced on the basis of the image in FIG. 1A which is identically reproduced as FIG. 2A (FIG. 6, block 20). An appropriate operator is the morphological gradient which provides the modulus of the gradient at each point (cf. Serra). The operator dilates and erodes the starting image in parallel, using a structuring element constituted by a diamond of size 1, and it subtracts one of the resulting images from the other.

Thereafter, the gradient image is modified by means of the binary image of the union of summits and thalwegs shown in FIG. 1E, thereby eliminating minima that are meaningless (FIG. 6, block 30). To do this, a dual reconstruction operation is performed (cf. Meyer et al.) between the gradient image and an image obtained from the union binary image: points of value 1 being transformed to points of value 0, and points of value 0 taking a value greater than the maximum of the gradient values. The resulting image is shown in FIG. 2C.

The following stage uses the gradient image as modified in this way in an operation for establishing divides (cf. Meyer et al.), thereby defining boundaries between the objects marked by the summits and the objects marked by the thalwegs (FIG. 6, block 40). This serves to establish outlines for vugs, as shown in FIG. 2D.

FIGS. 3A to 3D show another form of processing for extracting connectivity between vugs from the image.

Figure 3:
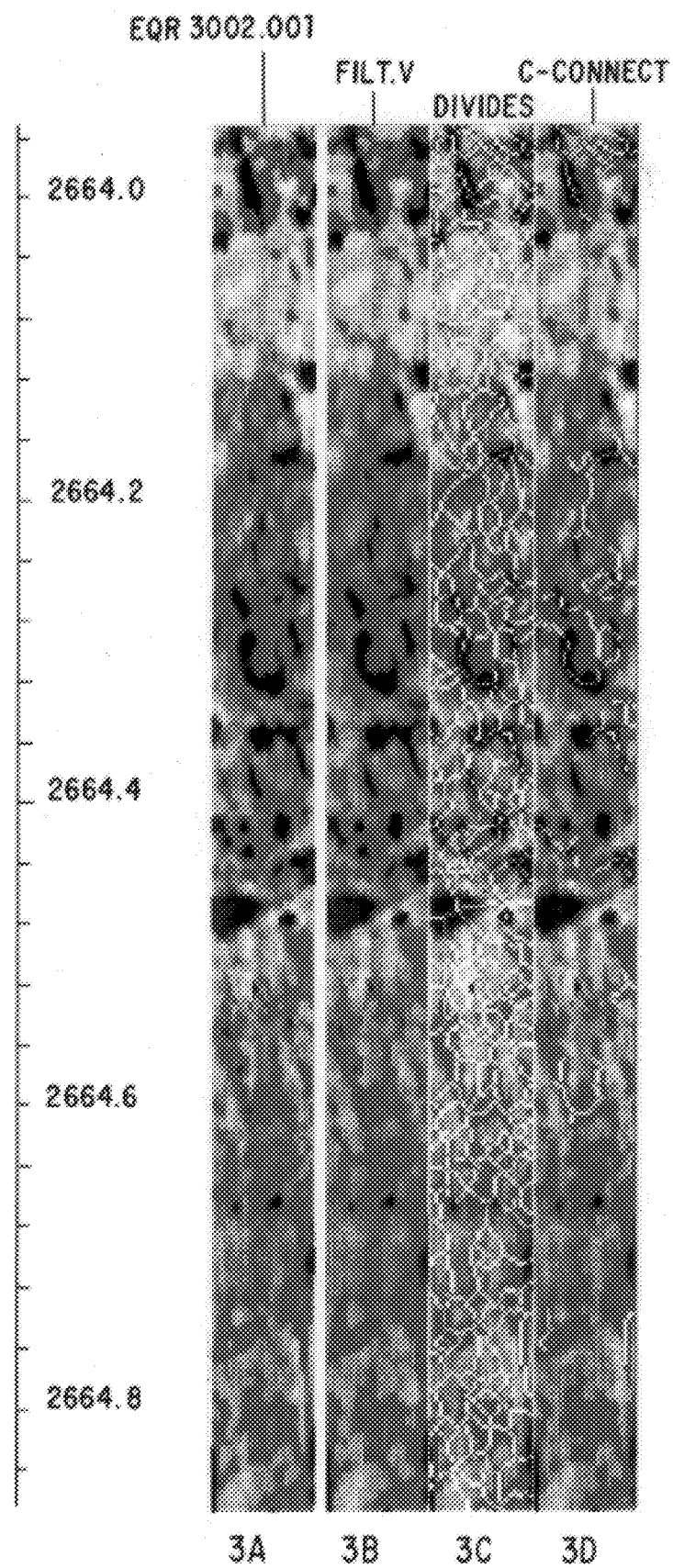
FIGS. 3A to 3D show the processing stages which lead to connections between vugs being shown up, with FIG. 3A reproducing the image of FIG. 1A.

FIG. 3A reproduces FIG. 1A and consequently shows the original image. FIG. 3B is identical to FIG. 1B and shows the image filtered in the manner described above. The operator providing the divides is then applied to the filtered image. The network of lines obtained in this way is shown in white on FIG. 3C, superimposed on the image of FIG. 3B. To provide an image which retains only connections between vugs, arcs having a conductivity value below a given threshold are eliminated, which threshold may be defined in an adaptive manner. The resulting image is shown in FIG. 3D.

Figure 4:
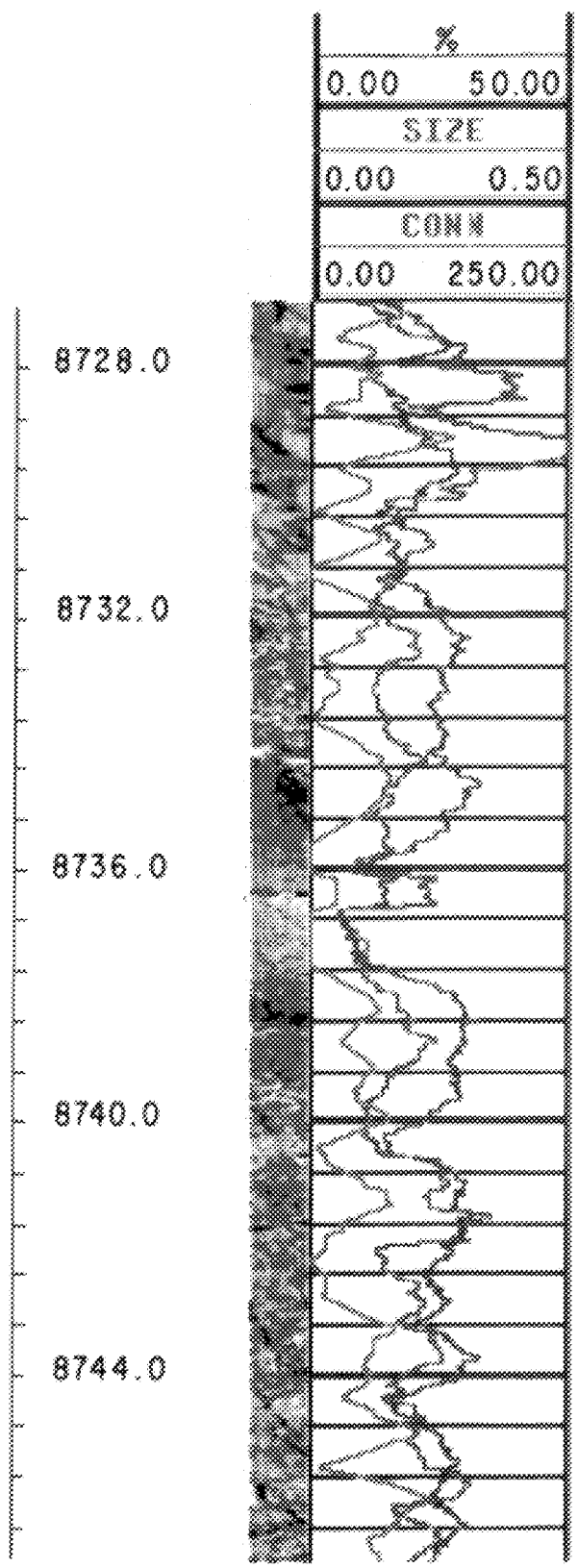
FIG. 4 is a graphical representation of attributes as derived from the above processing.

FIG. 4 shows how the images of FIGS. 2D and 3D can be used to obtain a graphical presentation in the longitudinal direction of the borehole showing attributes that characterize the texture heterogeneities of the geological formations (FIG. 6, block 50). The graphs (logs) shown in FIG. 4 correspond to the following attributes:

%=percentage of vugs (proportion of the area occupied by vugs relative to the total area of the image);

SIZE=mean vug size; and

CONN=degree of connectivity between vugs (defined as the mean of conductivity values at points belonging to the connections between vugs, as shown in FIG. 3D).

It should be observed that the invention is applicable to detecting objects other than vugs. For example, with appropriate inversions, the method described could be used for detecting high resistivity inclusions (nodules, pebbles).

In addition, the invention is not limited to use with an electrical image of the wall of a borehole. Images obtained by measuring other physical parameters of sub-surface formations could be used in the context of the invention providing they have suitable resolution.

We claim:

1. A method of characterizing texture heterogeneities of a structure in a geological formation traversed by a borehole, represented by an image of a circumferential segment of a borehole wall having variations in a physical parameter of the formation in the longitudinal direction of the borehole and around a periphery of a wall of the borehole, comprising the steps of:

a) obtaining signals representative of a two-dimensional reconstructed image of an in-situ section of an earth formation b) automatically processing the signals to extract from the image, by means of mathematical morphological operators, a further reconstructed image in which geological objects correspond to a determined morphological type of heterogeneity, defined as an enclosed zone having high value for said parameter, wherein said objects are present in such a way that said objects are capable of being automatically extracted from the further image thus produced to indicate a discontinuity within said structure corresponding to said enclosed zone; and c) determining the variation in the longitudinal direction of the borehole of at least one attribute defined for the morphological type of heterogeneity.

2. A method of characterizing texture heterogeneities of a structure in a geological formation traversed by a borehole, represented by an image of a circumferential segment of a borehole wall having variations in a physical parameter of the formation in the longitudinal direction of the borehole and around a periphery of a wall of the borehole, comprising the steps of:

1) automatically processing the image to extract from the image, by means of mathematical morphological operators, at least an image in which geological objects correspond to a determined morphological type of heterogeneity, defined as an enclosed zone having high value for said parameter wherein objects having a high value of said parameter or of a magnitude derived therefrom are marked, objects having a low value of said parameter or of a magnitude derived therefrom are marked, and the outlines of said objects are determined as a function of values for the gradient of said parameter in such a way that said objects are capable of being automatically extracted from the image thus produced to indicate a discontinuity within said structure corresponding to said enclosed zone; and 2) determining the variation in the longitudinal direction of the borehole of at least one attribute defined for the morphological type of heterogeneity.

3. A method according to claim 2, in which geological objects extracted from the image are vugs.

4. A method according to claim 1, in which geological objects extracted from the image are vugs.

5. A method according to claim 3, in which an attribute used is the proportion of the area of the image that is occupied by the vugs.

6. A method according to claim 3, in which an attribute used is the mean area of the vugs.

7. A method according to claim 6, in which an attribute used is the proportion of the area of the image that is occupied by the vugs.

8. A method according to claim 3, in which interconnection lines between vugs are also extracted from the image.

9. A method according to claim 5, in which interconnection lines between vugs are also extracted from the image.

10. A method according to claim 6, in which interconnection lines between vugs are also extracted from the image.

11. A method according to claim 8, in which the mean of the values of said parameter in the lines interconnecting the vugs is used as an attribute.

12. A method of characterizing texture heterogeneities of a structure in a geological formation traversed by a borehole, represented by an image of a circumferential segment of a borehole wall having variations in a physical parameter of the formation in the longitudinal direction of the borehole and around a periphery of a wall of the borehole, comprising the steps of:
   1) automatically processing the image to extract from the image, by means of mathematical morphological operators, at least an image in which;
      a) geological objects corresponding to a determined morphological type of heterogeneity are defined as an enclosed zone having high value for said parameter,
      b) geological objects having a high value of said parameter are indicated as vugs;
      c) , geological objects having a low value of said parameter are indicated as other than vugs; and
      d) outlines of said objects are determined as a function of values for the gradient of said parameter;
   wherein said vugs are present in such a way that said vugs are capable of being automatically extracted from the image thus produced to indicate a discontinuity within said structure corresponding to said enclosed zone; and
   2) determining the variation of one attribute of the vugs in the longitudinal direction of the borehole, said attribute relating to the area of the vugs.

13. The method of claim 12, said attribute relating to a proportion of an area of said image occupied by said vugs.

14. The method of claim 12, said attribute relating to the mean area of said vugs.

15. A method of characterizing a formation, the steps comprising:
   1) producing an image of a circumferential segment of a borehole wall having variations in a physical parameter of the formation in a longitudinal direction of the borehole and around a periphery of a wall of the borehole, wherein the image indicates the structure of the formation;
   2) using mathematical morphological operators to automatically process the image indicating the structure and automatically extract discontinuities in the structure;
   3) correlating high values of the parameter with vugs and correlating low values of the parameter with objects other than vugs;
   4) determining outlines of the vugs and objects other than vugs as a function of values of a gradient of the parameter,
   5) determining a variation of an attribute of the vugs in the longitudinal direction of the borehole;
   6) indicating discontinuities in the structure as the vugs in the formation based on the variation of the attribute of the vugs.

16. The method of claim 15, the attribute comprising a proportional area of the image which is occupied by the vugs.

17. The method of claim 15, the attribute comprising the mean area of the vugs.

18. A method according to claim 4, in which an attribute used is the proportion of the area of the image that is occupied by the vugs.

19. A method according to claim 4, in which an attribute used is the mean area of the vugs.

20. A method according to claim 19, in which an attribute used is the proportion of the area of the image that is occupied by the vugs.

21. A method according to claim 4, in which interconnection lines between vugs are also extracted from the image.

22. A method according to claim 18, in which interconnection lines between vugs are also extracted from the image.

23. A method according to claim 19, in which interconnection lines between vugs are also extracted from the image.

24. A method according to claim 21, in which the mean of the values of said parameter in the lines interconnecting the vugs is used as an attribute.

* * * * *